United States Patent
Ravishankar et al.

(10) Patent No.: US 10,851,273 B2
(45) Date of Patent: Dec. 1, 2020

(54) MOLECULAR GELATORS AND USES THEREOF

(71) Applicant: Hindustan Petroleum Corporation LTD., Mumbai (IN)

(72) Inventors: Raman Ravishankar, Bengaluru (IN); Siva Kesava Raju Chinthalapati, Bengaluru (IN); Bhaskar Pramanik, Bengaluru (IN); Tanmoy Kar, Bengaluru (IN); Peddi Venkat Chalapathi Rao, Bengaluru (IN); Venkateswarlu Choudary Nettem, Bengaluru (IN)

(73) Assignee: Hindustan Petroleum Corporation LTD., Mumbai (IN)

( * ) Notice: Subject to any disclaimer, the term of this patent is extended or adjusted under 35 U.S.C. 154(b) by 0 days.

(21) Appl. No.: 15/778,923

(22) PCT Filed: Nov. 29, 2016

(86) PCT No.: PCT/IN2016/050424
§ 371 (c)(1),
(2) Date: May 24, 2018

(87) PCT Pub. No.: WO2017/138013
PCT Pub. Date: Aug. 17, 2017

(65) Prior Publication Data
US 2018/0346780 A1    Dec. 6, 2018

(30) Foreign Application Priority Data
Feb. 12, 2016  (IN) .............................. 201621005085

(51) Int. Cl.
| | |
|---|---|
| *C09K 3/32* | (2006.01) |
| *C07K 5/062* | (2006.01) |
| *C07K 5/065* | (2006.01) |
| *C07K 5/078* | (2006.01) |
| *B01D 17/02* | (2006.01) |
| *C07C 237/22* | (2006.01) |

(52) U.S. Cl.
CPC ................ *C09K 3/32* (2013.01); *B01D 17/02* (2013.01); *C07C 237/22* (2013.01); *C07K 5/0606* (2013.01); *C07K 5/06017* (2013.01); *C07K 5/06052* (2013.01); *C07K 5/06078* (2013.01); *C07K 5/06165* (2013.01)

(58) Field of Classification Search
CPC ................ C09K 3/32; C07C 237/22
See application file for complete search history.

(56) References Cited

U.S. PATENT DOCUMENTS

| | | | |
|---|---|---|---|
| 3,985,722 A | 10/1976 | Yoshida et al. | |
| 10,343,144 B2* | 7/2019 | Ravishankar | C02F 1/285 |
| 2011/0287929 A1* | 11/2011 | Smith | C08J 9/00 |
| | | | 502/402 |
| 2012/0074067 A1* | 3/2012 | Podella | C02F 1/681 |
| | | | 210/668 |
| 2012/0201863 A1* | 8/2012 | John | A61K 8/60 |
| | | | 424/400 |
| 2019/0106399 A1* | 4/2019 | Ravishankar | B01D 17/047 |
| 2019/0241580 A1* | 8/2019 | Ravishankar | C02F 1/285 |

FOREIGN PATENT DOCUMENTS

| | | |
|---|---|---|
| CN | 102199194 A | 9/2011 |
| EP | 3098232 A1 | 11/2016 |
| WO | 03068141 A2 | 8/2003 |

OTHER PUBLICATIONS

International Search Report, issued by the Indian Patent Office for PCT/IN2016/050424, dated Feb. 20, 2017.
Kar, et al., Organogelation and Hydrogelation of Low-Molecular-Weight Amphiphilic Dipeptides: pH Responsiveness in Phase-Selective Gelatin and Dye Removal, American Chemical Society, vol. 25, No. 15, p. 8639-8648, 2009.
Kar, et al., pH-Triggered conversion of soft nanocomposites: in situ synthesized AuNP-hydrogel to AuNP-organogel, Soft Matter, vol. 6, No. 19, p. 4777, 2010.
Mandal, et al., The striking influence of SWNT-COOH on self-assembled gelation, Chemical COmmunications, vol. 48, No. 12, p. 1814-1816, 2011.
Jadhav, et al., Sugar-Derived Phase-Selective Molecular Gelators as Model Solidifiers for Oil Spills, Angewandte Chemie International Edition, vol. 49, No. 42, p. 7695-7698, 2010.

\* cited by examiner

*Primary Examiner* — Ellen M McAvoy
(74) *Attorney, Agent, or Firm* — Thomas|Horstemeyer, LLP

(57) ABSTRACT

In accordance with the present subject matter there is provided a compound of Formula I wherein, $R_1$ is substituted $C_1$ to $C_{10}$ alkyl; and $R_2$ is substituted $C_1$ to $C_{10}$ alkyl, a process for preparing a compound of Formula I, and a gel comprising a compound of Formula I. There is also provided a process for separating a hydrophobic material from a mixture of hydrophobic and hydrophilic material using a compound of Formula I.

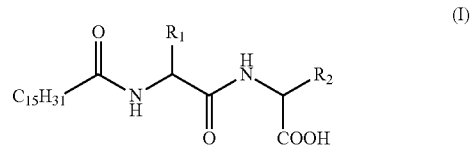

10 Claims, No Drawings

MOLECULAR GELATORS AND USES THEREOF

TECHNICAL FIELD

The subject matter described herein in general relates to peptide-based compounds that are able to form gels. The subject matter further relates to methods of making peptide-based compounds, gels including such compounds. The subject matter also relates to a process for separating hydrophobic material from a mixture of hydrophobic and hydrophilic material.

BACKGROUND

A gel can be defined as a solution in which the solid, also known as a gelator, is meshed to form a rigid or semi-rigid mixture results. Depending on the structural nature of gel networks, gels can be simply divided into chemical gels and physical gels. In the case of chemical gels, the aggregation units at different levels are connected into three-dimensional networks via covalent bonds whereas in physical gels, the molecules of a gelator aggregate into network structure via various non-covalent interactions, which are considerably weaker than covalent bonds.

Physical gelation of water and solvents include polymers, micro- or nano-particles, and low-molecular mass organic compounds (LMMGs). The gels formed by latter are named supramolecular gels or molecular gels and can be used for gelation of oil from oil-water mixtures for oil spill recovery. The spilled oil is transformed from a liquid into semi-solid or rubber-like materials floating on the surface of water by introducing LMMGs into the oil contaminated water.

Jadhav and co-workers have disclosed a new class of sugargelators that can selectively gel (solidify) the oil phase from an oil-water mixture at room temperature. The process for preparation of gelators is easy and environmentally benign. Further, the gelators can be recovered and reused multiple times (Angew. Chem. Int. Ed. 2010, 49, 7695-7698).

SUMMARY

The present disclosure relates to a compound having the Formula I:

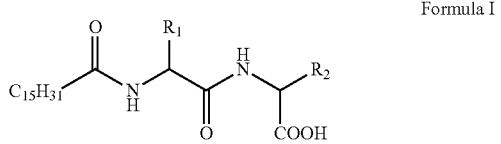

Formula I wherein $R_1$ is substituted $C_1$ to $C_{10}$ alkyl; $R_2$ is substituted $C_1$ to $C_{10}$ alkyl.

The present disclosure also relates to a process for preparing the compound of Formula I.

The present disclosure further relates to a gel comprising a compound of Formula I and a hydrophobic material.

The present disclosure further relates to a process for separating a hydrophobic material from a mixture of hydrophobic and hydrophilic material, said process comprising the steps of: (a) contacting a compound of Formula I with a mixture of hydrophobic and hydrophilic material to obtain a gel comprising the hydrophobic material and a residue of hydrophilic material; (b) separating the gel from the residue of hydrophilic material; (c) heating the gel to obtain the hydrophobic material and to reclaim the compound of Formula I.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "hydrocarbon(s)" refers to organic compounds that are made of hydrogen and carbon atoms. The source of the hydrocarbons may be from crude oils and refined petroleum products. Crude oil and other petroleum fractions may include compounds with hetero atoms like nitrogen, oxygen, sulfur, halogens and metallic elements along with hydrocarbons.

The term "gel" refers to a colloidal suspension of a solid dispersed in liquid and appear like semi solid.

The term "CRN" means cracked run naptha (mainly comes from the Fluidized Catalytic Cracking (FCC) unit in the refinery).

The term "SRN" means straight run naphtha, which comes from direct distillation of crude oil.

The term "diesel" means a specific fractional distillate of petroleum crude oil between 200° C. and 350° C. at atmospheric pressure.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 140° C. to about 180° C. should be interpreted to include not only the explicitly recited limits of about 140° C. to about 180° C., but also to include sub-ranges, such as 145° C. to 155° C., 150° C. to 170° C., and so forth, as well as individual amounts, including fractional amounts, within the specified ranges, such as 142.2° C., 140.6° C., and 141.3° C., for example.

The present disclosure relates to gelators which can be used for oil or hydrocarbon removal from water. These absorbed hydrocarbons can be easily recovered from the gel including the amphiphilic gelators and oil by heating the gel. The gelators have the potential for selective extraction of oil in water systems and water in oil systems.

In one implementation, the present disclosure relates to a compound of Formula I

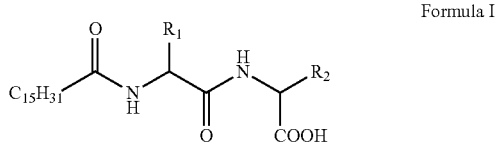

Formula I wherein $R_1$ is an optionally substituted straight or branched chain $C_1$ to $C_{10}$ alkyl; and $R_2$ is an optionally substituted straight or branched chain $C_1$ to $C_{10}$ alkyl.

In one implementation, the present disclosure relates to a compound of Formula I, wherein $R_1$ is substituted $C_1$ to $C_{10}$ alkyl; $R_2$ is substituted $C_1$ to $C_{10}$ alkyl.

In one implementation, the present disclosure relates to a compound of Formula I, wherein $R_1$ and $R_2$ are independently selected from $C_1$ to $C_5$ alkyl substituted with $C_1$ to $C_3$ alkyl, $C_5$-$C_{10}$ aryl, $C_6$-$C_{10}$ heteroaryl, or a heteroatom selected from the group consisting of O, N, and S, wherein the heteroatom is further substituted with $C_1$ to $C_3$ alkyl, $C_5$-$C_{10}$ aryl, or $C_6$-$C_{10}$ heteroaryl.

In one implementation, the present disclosure relates to a compound of Formula I, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or a heteroatom selected from the group consisting of O, N, and S, wherein the heteroatom is further substituted with $C_1$ to $C_2$ alkyl, $C_5$-$C_{10}$ aryl, or $C_6$-$C_{10}$ heteroaryl.

In one implementation, the present disclosure relates to a compound of Formula I, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or a heteroatom selected from the group consisting of O, N, and S, wherein the heteroatom is further substituted with $C_1$ to $C_2$ alkyl.

In one implementation, the present disclosure relates to a compound of Formula I, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or S substituted with $C_1$ to $C_2$ alkyl, wherein both $R_1$ and $R_2$ are not $C_1$ to $C_3$ alkyl substituted with S substituted with $C_1$ to $C_2$ alkyl.

In one implementation, the present disclosure relates to a compound of Formula I, wherein $R_1$ and $R_2$ are independently selected from $C_1$ to $C_2$ alkyl substituted with $C_1$ alkyl, $C_6$ aryl, $C_8$ heteroaryl with N as the heteroatom, or S further substituted with $C_1$ alkyl, wherein both $R_1$ and $R_2$ are not $C_1$ to $C_2$ alkyl substituted with S substituted with $C_1$ alkyl.

In one implementation, the present disclosure relates to a compound of Formula I, wherein $R_1$ and $R_2$ are independently selected from $C_1$ to $C_3$ alkyl substituted with $C_1$ to $C_2$ alkyl, or S further substituted with $C_1$ to $C_2$ alkyl, wherein both $R_1$ and $R_2$ are not $C_1$ to $C_3$ alkyl substituted with S further substituted with $C_1$ to $C_2$ alkyl.

In one implementation, the present disclosure relates to a compound of Formula I, wherein $R_1$ is $C_1$ to $C_3$ alkyl substituted with $C_1$ to $C_2$ alkyl, and $R_2$ is $C_1$ to $C_3$ alkyl substituted with S further substituted with $C_1$ to $C_2$ alkyl.

In one implementation, the present disclosure relates to a compound of Formula I, wherein $R_1$ is $C_2$ alkyl substituted with $C_1$ alkyl, and $R_2$ is $C_2$ alkyl substituted with S substituted with $C_1$ alkyl.

In one implementation, the present disclosure relates to a compound of Formula I, wherein $R_1$ is a branched chain $C_1$ to $C_5$ alkyl.

In one implementation, the present disclosure relates to a compound of Formula I, wherein $R_1$ is a straight chain $C_1$ to $C_5$ alkyl substituted with X, wherein X is selected from the group consisting of heteroatom S which is further substituted with $C_1$ to $C_3$ alkyl, a $C_5$-$C_{10}$ aryl, a $C_6$-$C_{10}$ heteroaryl wherein the heteroatom is selected from the group consisting of O, N, and S, or combinations thereof.

In one implementation, the present disclosure relates to a compound of Formula I, wherein $R_2$ is a straight or branched chain $C_1$ to $C_5$ alkyl.

In one implementation, the present disclosure relates to a compound of Formula I, wherein $R_2$ is a straight chain $C_1$ to $C_5$ alkyl substituted with X, wherein X is selected from the group consisting of heteroatom S which is further substituted with $C_1$ to $C_3$ alkyl, a $C_5$-$C_{10}$ aryl, and combinations thereof.

In one implementation, the present disclosure relates to a compound of Formula I, wherein $R_1$ is a branched chain $C_3$ alkyl.

In one implementation, the present disclosure relates to a compound of Formula I, wherein $R_1$ is a $C_2$ alkyl substituted with heteroatom S which is further substituted with $C_1$ alkyl and $R_2$ is not a straight chain $C_2$ alkyl substituted with heteroatom S which is further substituted with $C_1$ alkyl.

In one implementation, the present disclosure relates to a compound of Formula I, wherein $R_1$ is $C_1$ alkyl substituted with $C_6$ aryl.

In one implementation, the present disclosure relates to a compound of Formula I, wherein R1 is $C_1$ alkyl substituted with $C_9$ heteroaryl wherein the heteroatom is N.

In one implementation, the present disclosure relates to a compound of Formula I, wherein $R_2$ is a branched chain $C_3$ alkyl.

In one implementation, the present disclosure relates to a compound of Formula I, wherein $R_2$ is $C_1$ alkyl.

In one implementation, the present disclosure relates to a compound of Formula I, wherein $R_2$ is $C_1$ alkyl substituted with $C_6$ aryl.

In one implementation, the present disclosure relates to a compound of Formula I, wherein $R_2$ is a $C_2$ alkyl substituted with heteroatom S which is further substituted with $C_1$ alkyl and $R_1$ is not a $C_2$ alkyl substituted with heteroatom S which is further substituted with $C_1$ alkyl.

In one implementation, the present disclosure relates to a compound of Formula I, wherein $R_1$ is a branched chain $C_3$ alkyl and $R_2$ is a $C_2$ alkyl substituted with heteroatom S which is further substituted with $C_1$ alkyl.

In one implementation, the present disclosure relates to a compound of Formula I, wherein $R_1$ is a $C_2$ alkyl substituted with heteroatom S which is further substituted with $C_1$ alkyl and $R_2$ is a branched chain $C_3$ alkyl.

In one implementation, the present disclosure relates to a compound of Formula I, wherein $R_1$ is a branched chain $C_3$ alkyl and $R_2$ is a branched chain $C_3$ alkyl.

In one implementation, the present disclosure relates to a compound of Formula I, wherein $R_1$ is a $C_1$ alkyl substituted with $C_6$ aryl and $R_2$ is $C_1$ alkyl.

In one implementation, the present disclosure relates to a compound of Formula I, wherein $R_1$ is $C_1$ alkyl substituted with $C_6$ aryl and $R_2$ is $C_1$ alkyl substituted with $C_6$ aryl.

In one implementation, the present disclosure relates to a compound of Formula I, wherein $R_1$ is $C_1$ alkyl substituted with $C_9$ heteroaryl wherein the heteroatom is N and $R_2$ is $C_1$ alkyl substituted with $C_6$ aryl.

In one implementation, the present disclosure relates to compounds of Formula I, wherein the compounds are selected from compounds 1-7.

The representative compounds of Formula I are:

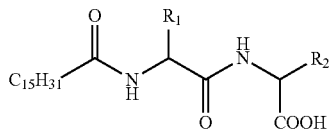

| Compound | $R_1$ | $R_2$ |
|---|---|---|
| 1 | $CH_2CH_2SCH_3$ | $CH_2CH_2SCH_3$ |
| 2 | $CH(Me)_2$ | $CH_2CH_2SCH_3$ |
| 3 | $CH_2CH_2SCH_3$ | $CH(Me)_2$ |
| 4 | $CH(Me)_2$ | $CH(Me)_2$ |
| 5 | $CH_2Ph$ | $CH_3$ |
| 6 | $CH_2Ph$ | $CH_2Ph$ |
| 7 | (3-methylindole) | $CH_2Ph$ |

In one implementation, the present disclosure relates to a process for preparing the compounds of Formula I.

In one implementation, the compounds of Formula I and gels synthesized therefrom can be used in such applications as tissue engineering, drug delivery, separation of biomolecules, and stimulus-responsive advanced materials. The compounds of Formula I can be used to form gels having numerous applications.

In one implementation, the present disclosure relates to a gel comprising compounds of Formula I and a hydrophobic material.

In one implementation, the hydrophobic material is oil selected from the group consisting of synthetic oil, natural oil, crude oil, fuel oil, petroleum fractions, and combinations thereof. In another implementation, oil can be selected from the group consisting of SRN, CRN, diesel, crude oil, vegetable oil, and combinations thereof.

In another implementation, the compounds of Formula I can be added to a solvent in order to produce a gel. The term solvent refers to a polar solvent, non-polar solvent and mixtures thereof. Solvents can be nonpolar such as, for example, hydrocarbons like pentane, cyclopentane, hexane, cyclohexane, benzene, toluene, xylene, 1,4-dioxane, chloroform, diethyl ether or mixtures thereof. In one implementation, the solvents can be polar, aprotic solvents such as, for example, dichloromethane, tetrahydrofuran, ethyl acetate, acetone, dimethylformamide, acetonitrile, pyridine, carbon disulfide, benzonitrile, or dimethyl sulfoxide. In another implementation, the solvent can be polar protic solvents such as alcohols and carboxylic acids including, but not limited to, formic acid, n-butanol, isopropanol, n-propanol, ethanol, methanol, acetic acid, ethylene glycol, propylene glycol, glycerin, or water. Mixtures of solvents can also be used herein. In another implementation, the solvent is a hydrocarbon.

In one implementation, the present disclosure relates to a process for separating a hydrophobic material from a mixture of hydrophobic and hydrophilic material, said process comprising the steps of: (a) contacting a compound of Formula I with a mixture of hydrophobic and hydrophilic material to obtain a gel comprising the hydrophobic material and a residue of hydrophilic material; (b) separating the gel from the residue of hydrophilic material; (c) heating the gel to obtain the hydrophobic material and to reclaim the compound of Formula I.

In one implementation, the present disclosure relates to a process for separating a hydrophobic material from a mixture of hydrophobic and hydrophilic material, wherein the hydrophobic material is oil selected from the group of synthetic oil, natural oil, crude oil, fuel oil, petroleum fractions, and combinations thereof.

In one implementation, the present disclosure relates to a process for separating a hydrophobic material from a mixture of hydrophobic and hydrophilic material, wherein the hydrophilic material is selected from the group consisting of water, polar solvents, salt solution, and combinations thereof.

In one implementation, the present disclosure relates to a process for separating a hydrophobic material from a mixture of hydrophobic and hydrophilic material, wherein the compounds of Formula I is contacted with a mixture of hydrophobic and hydrophilic material. The concentration of the compound of Formula I in the mixture of hydrophobic and hydrophilic material is in the range of 0.1-10%. In one implementation, the concentration of the compound of Formula I in the mixture of hydrophobic and hydrophilic material is in the range of 1-5%.

In one implementation, the present disclosure relates to a process for separating a hydrophobic material from a mixture of hydrophobic and hydrophilic material, wherein the compound of Formula I and the mixture of hydrophobic and hydrophilic material is heated to a temperature of 70 to 80° C., followed by cooling to obtain a gel and a residue of hydrophilic material.

In one implementation, the present disclosure relates to a process for separating a hydrophobic material from a mixture of hydrophobic and hydrophilic material, wherein the gel is separated from the hydrophilic material.

In one implementation, the present disclosure relates to a process for separating a hydrophobic material from a mixture of hydrophobic and hydrophilic material, wherein the gel is heated to a temperature based upon the boiling point of gelated hydrophobic material e.g. 110° C. for toluene, 180° C. for SRN to obtain the hydrophobic material and to reclaim the compound of Formula I.

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

Synthesis of Compounds of Formula I

The compounds of Formula I was synthesized according to Scheme 1.

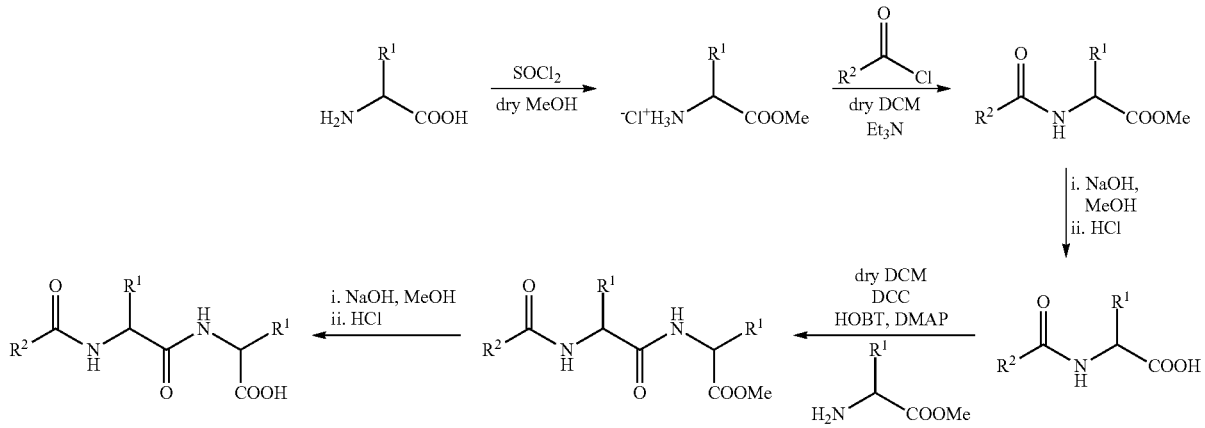

Scheme 1

Amino acid based amphiphiles were synthesized by conventional solution phase methodology as represented by Scheme 1. Briefly, the methyl ester (1 equiv) of an amino acid was coupled with palmitic acid chloride (1 equiv) in dry chloroform in presence of $Et_3N$. The ester-protected long-chain amide or monopeptide was then purified through column chromatography using 60-120 mesh silica gel and ethyl acetate/hexane as the eluent. The product was hydrolyzed using 1 N NaOH (1.1 equiv) in MeOH for 6 h with stiffing at room temperature. Solvents were removed on a rotary evaporator, and the mixture was extracted in DCM following acidification by 1 N HCl to get the corresponding monopeptide carboxylic acid. This monopeptide acid (1 equiv) was then coupled with another methyl ester protected amino acid (1.1 equiv) using DCC (1.1 equiv) in dry dichloromethane (DCM) in presence of HOBT (1.1 equiv) and DMAP (1.1 equiv). The purified product was obtained by column chromatography using 60-120 mesh silica gel and ethyl acetate/toluene as the eluent. The product was then subjected to hydrolysis by 1 N NaOH (1.1 equiv) in MeOH for 6 h followed by HCl and the final dipeptide carboxylic acid was obtained following column chromatographic separation using DCM-MeOH as eluent.

Compound 1 was synthesized by following the procedure as described above using 60 mmol of Methionine and 30 mmol of palmitic acid. Yield: 72%. ESI-MS (+Ve): m/z: 541.4296 $[C_{26}H_{50}N_2O_4S_2Na^+]$, (calculated): 541.3065 $[M+Na^+]$.

Compound 2 was synthesized by following the procedure as described for compound 1; however, using 30 mmol of Valine and 30 mmol of palmitic acid followed by 30 mmol of Methionine instead 60 mmol of Methionine. Yield: 71%. ESI-MS (+Ve): m/z: 509.3852 $[C_{26}H_{50}N_2O_4SNa^+]$, (calculated): 509.3344 $[M+Na^+]$.

Compound 3 was synthesized by following the procedure as described for compound 2; however, using 30 mmol of Methionine and Valine in reverse order with 30 mmol of palmitic acid. Yield: 66.8%. ESI-MS (+Ve): m/z: 509.3836 $[C_{26}H_{50}N_2O_4SNa^+]$, (calculated): 509.3344 $[M+Na^+]$.

Compound 4 was synthesized by following the procedure as described for compound 1 however, using 60 mmol of Valine instead of Methionine. Yield: 79.4%. ESI-MS (+Ve): m/z: 477.1625 $(C_{26}H_{50}N_2O_4Na^+)$, (calculated): 476.6680 $[M+Na^+]$.

Compound 5 was synthesized by following the procedure as described for compound 1; however, using 30 mmol of Phenylalanine and 30 mmol of palmitic acid followed by 30 mmol of Alanine. Yield: 75.9%. ESI-MS (+Ve): m/z: 497.2073 $[C_{28}H_{46}N_2O_4Na^+]$, (calculated): 497.3458 $[M+Na^+]$.

Compound 6 was synthesized by following the procedure as described for compound 1 however, using 60 mmol of Phenylalanine instead of Methionine. Yield: 68.8%. ESI-MS (+Ve): m/z: 573.1619 $[C_{34}H_{50}N_2O_4Na^+]$, (calculated): 573.3771 $[M+Na^+]$.

Compound 7 was synthesized by following the procedure as described for compound 1; however, using 30 mmol of Tryptophan and 30 mmol of palmitic acid followed by 30 mmol of Phenylalanine. Yield: 73.6%. ESI-MS (+Ve): m/z: 612.5449 $[C_{36}H_{51}N_3O_4Na^+]$, (calculated): 612.3880 $[M+Na^+]$.

Example 2

Gelation Study with Crude Oil

In a typical procedure, the gelator compound of Formula I was added to 0.5 ml of crude oil in a glass vial with an internal diameter (i.d.) of 10 mm. The mixture was warmed gently to dissolve the solid compound in crude oil. Then the solution was allowed to cool slowly to room temperature without disturbance. After few minutes, the solid aggregate mass was found to be stable to inversion of the glass vial, and then the compound was recognized to form a gel.

To calculate minimum gelation concentration (MGC), gelator is added gradually from 1 mg to higher amount in required solvent/oil (0.5 ml) and the above process (heating and cooling) was repeated until gel was formed. MGC is the amount in grams of gelator required for 100 ml of solvent/oil to be gelated. Minimum Uptake Capability (MUC) was also calculated which is volume in ml of solvent/oil gelated by 1 g of gelator.

Gelation Study with Other Oils and Solvents

The gelation process for crude oil was repeated taking CRN, SRN and Diesel as refinery distillates and taking hexane, octane, dodecane, hexadecane, benzene, toluene and xylene as solvents (Table 1-3).

TABLE 1

Gelation abilities of compound of Formula I in different hydrocarbon solvents

| | Compound | | | | | | | | | | | | | |
|---|---|---|---|---|---|---|---|---|---|---|---|---|---|---|
| | 1 | | 2 | | 3 | | 4 | | 5 | | 6 | | 7 | |
| | MGC (% w/v) | MUC | MGC (% w/v) | MUC | MGC (% w/v) | MUC | MGC (% w/v) | MUC | MGC (% w/v) | MUC | MGC (% w/v) | MUC | MGC (% w/v) | MUC |
| Hexane | 1.1 | 90 | 1.1 | 90 | 1.15 | 86 | 1.14 | 87 | 1.1 | 90 | I | ... | I | ... |
| Octane | 0.8 | 125 | 0.89 | 112 | 0.9 | 111 | 0.9 | 111 | 1.02 | 98 | 2.1 | 47 | I | ... |
| Dodecane | 0.7 | 142 | 0.74 | 135 | 0.75 | 133 | 0.74 | 135 | 0.65 | 153 | 1.22 | 81 | P | ... |
| Hexadecane | 0.6 | 166 | 0.72 | 138 | 0.7 | 142 | 0.81 | 123 | 0.4 | 250 | 0.95 | 105 | 1.6 | 62 |
| Benzene | 0.85 | 117 | 0.85 | 117 | 0.89 | 112 | 0.9 | 111 | S | ... | S | ... | 0.67 | 149 |
| Toluene | 0.7 | 142 | 0.8 | 125 | 0.84 | 119 | 0.9 | 111 | S | ... | S | ... | 0.6 | 166 |
| Xylene | 0.7 | 142 | 0.85 | 117 | 0.82 | 121 | 0.9 | 111 | S | ... | S | ... | 0.6 | 166 |

MGC = Minimum Gelation Concentration,
MUC = Minimum Uptake Capability,
S = Soluble,
I = Insoluble,
P = Precipitate Gelation ability of the compounds is tabulated in the above table. Surprisingly, compounds 1-5 are more susceptible to form gel with the paraffinic solvents. Whereas for compounds 6 and 7, gelation ability towards paraffinic solvents are poor; 7 can form gel with hexadecane only. All these gelators are capable to form gel with aromatic solvents and their gelation ability also follow the same trend as described above.

gelation ability is observed for diesel (75 to 250 times). On going from 1 to 4, a gradual decrease in the gelation ability is observed (MGC for crude oil: 2 for 1 and 2.5 for 4). Gelation ability of 5, surprisingly, was observed to have maximum MGC (0.85) than others. However, on moving from compound 5 to 7, gelation ability gradually decreases. Compound 6 and 7 do not form gel with CRN and SRN. Gelation ability of 1-4 with paraffinic solvents are also

TABLE 2

Gelation abilities of compound of Formula I in different oils

| | Compound | | | | | | | | | | | | | |
|---|---|---|---|---|---|---|---|---|---|---|---|---|---|---|
| | 1 | | 2 | | 3 | | 4 | | 5 | | 6 | | 7 | |
| | MGC (% w/v) | MUC | MGC (% w/v) | MUC | MGC (% w/v) | MUC | MGC (% w/v) | MUC | MGC (% w/v) | MUC | MGC (% w/v) | MUC | MGC (% w/v) | MUC |
| CRN | 1 | 100 | 1.2 | 83 | 1.2 | 83 | 1.4 | 71 | 0.43 | 232 | S | ... | P | ... |
| SRN | 0.8 | 125 | 1 | 100 | 1.1 | 90 | 1.1 | 90 | 0.39 | 256 | 0.99 | 101 | P | ... |
| Diesel | 1 | 100 | 1.1 | 90 | 1.1 | 90 | 1.3 | 76 | 0.39 | 256 | 0.46 | 217 | 1.42 | 70 |
| Crude oil | 2 | 50 | 2.2 | 45 | 2.3 | 43 | 2.5 | 40 | 0.85 | 117 | 1.12 | 89 | 1.46 | 68 |
| Vegetable oil | 0.9 | 111 | 1.02 | 98 | 1.15 | 86 | 1.12 | 89 | 0.5 | 200 | 1.06 | 94 | 1.01 | 99 |

MGC = Minimum Gelation Concentration,
MUC = Minimum Uptake Capability,
S = Soluble,
I = Insoluble,
P = Precipitate The above table exhibit that gelator compounds are capable in transforming crude oil into gel phase with varying MGC values. Along with crude oil, different refinery fractions are also form gel by the gelator compounds as depicted in Table 2. Minimum uptake capability of crude oil was found be from 40 times 120 times whereas maximum reflected on the gelation ability with refinery distillates. Gelation ability of these compounds also tested for vegetable oil and all these gelators displayed very good gelator capability comparable to that of diesel. Gelation ability for refinery distillates found to be superior to that of crude oil as expected, as crude oil composition is very complex.

TABLE 3

Gelation abilities of compound of Formula I in different crude oils

| | Compound | | | | | | | | | | | | | |
|---|---|---|---|---|---|---|---|---|---|---|---|---|---|---|
| | 1 | | 2 | | 3 | | 4 | | 5 | | 6 | | 7 | |
| | MGC (% w/v) | MUC | MGC (% w/v) | MUC | MGC (% w/v) | MUC | MGC (% w/v) | MUC | MGC (% w/v) | MUC | MGC (% w/v) | MUC | MGC (% w/v) | MUC |
| (C1, API = 18.8) | 2.15 | 46 | 2.11 | 47 | 2.11 | 47 | 2.2 | 45 | 1.33 | 75 | 1.44 | 69 | 2.65 | 37 |
| (C2, API = 27.1) | 2 | 50 | 2.1 | 47 | 2.07 | 48 | 2.11 | 47 | ... | ... | 1.47 | 68 | 2.1 | 47 |
| (C3, API = 28.1) | 1.91 | 52 | 1.9 | 52 | 1.95 | 51 | 1.99 | 50 | ... | ... | 1.44 | 69 | 2.11 | 47 |
| (C4, API = 35.5) | 1.8 | 55 | 1.85 | 54 | 1.86 | 53 | 1.9 | 52 | 0.85 | 117 | 1.12 | 89 | 1.46 | 68 |
| (C5, API = 40.5) | 1.75 | 57 | 1.82 | 54 | 1.84 | 54 | 1.83 | 54 | ... | | 1.08 | 92 | 2.04 | 49 |

MGC = Minimum Gelation Concentration,
MUC = Minimum Uptake Capability,
S = Soluble,
I = Insoluble,
P = Precipitate In order to check the effect of the composition of crude oil on the gelation ability of the organogelator, experiments were conducted with crudes with varying API gravities ranging from very low API (C1, 18.8°) to high API (C5, 40.5°). Table 3 describes the effect of API gravity (crude composition) on the uptake (MGC) capability of the gelators. Highest gelation ability is again exhibited by 5 and decreasing order of gelation ability of 1 to 4 for other oils/solvents is followed here also. It could be observed that heavy crude (lower API) exhibited higher MGC and lighter crude (higher API) had lower MGC and the uptake capability decreased with increase in API gravity, thereby indicating the composition of crude also played a major role in the uptake by the gelator. Higher the resins & asphaltenes in the crude, lower the API gravity, thereby a reduction in the uptake capacity by the gelators was observed. This trend is discontinued for 7 going from API 35.5 to 40.5. The ease of formation of gel with lighter crude oil by the gelators compared to the heavier crude could be attributed to the higher paraffinic nature of the crude oil. Nevertheless, the gelators was found to be efficient and MGC of very low API (heaviest) crude was 2.65 wt % which is very remarkable. This study clearly indicated that the gelator could be used for the most of the crudes covering the wide spectrum of crude basket available from different parts of the globe.

Example 3

Selective Gelation of Crude Oil from a Biphasic Mixture of Oil and Water

In a typical procedure, 0.5 mL of crude oil and 0.5 mL of water were taken in a sample tube to which required amount of the gelator compounds of Formula I (as required to attain at least MGC) was added (Table 2). The gelator was then solubilized in this two-phase solution by heating. After the mixture was cooled to room temperature, the crude oil layer was gelated, keeping the water layer intact in the liquid state. The same process was followed for other oils like CRN, SRN and diesel.

TABLE 4

Gelation abilities of compound of Formula I in various oil-water mixtures

| | Compound | | | | | | | | | | | | | |
|---|---|---|---|---|---|---|---|---|---|---|---|---|---|---|
| | 1 | | 2 | | 3 | | 4 | | 5 | | 6 | | 7 | |
| | MGC (% w/v) | MUC | MGC (% w/v) | MUC | MGC (% w/v) | MUC | MGC (% w/v) | MUC | MGC (% w/v) | MUC | MGC (% w/v) | MUC | MGC (% w/v) | MUC |
| Crude-water | 2 | 50 | 2.2 | 45 | 2.3 | 43 | 2.5 | 40 | 1 | 100 | 1.2 | 83 | 1.5 | 66 |
| CRN-Water | 1.2 | 83 | 1.3 | 76 | 1.3 | 76 | 1.4 | 71 | 0.5 | 200 | S | ... | P | ... |
| SRN-Water | 1 | 100 | 1.2 | 83 | 1.2 | 83 | 1.3 | 76 | 0.4 | 250 | 1.2 | 83 | P | ... |
| Diesel-Water | 1.2 | 83 | 1.2 | 83 | 1.3 | 76 | 1.3 | 76 | 0.4 | 250 | 0.55 | 181 | 1.6 | 62 |

MGC = Minimum Gelation Concentration,
MUC = Minimum Uptake Capability,
S = Soluble,
I = Insoluble,
P = Precipitate Selective gelation of petroleum products from a biphasic mixture of oil and water was performed and the results are noted in Table 4. Gelator compounds were able to gelate exclusively the oil phase without altering the water phase during performance evaluation gelation experiments. Gelation ability of the compounds follow the same order as reported in Table 2 and no significant changes in the gelation ability in the biphasic mixture were noticed from that of individual oils. MGCs for SRN, SRN and diesel were increased by maximum 0.2% (w/v) from their respective individual/single phase studies.

Example 4

Selective Gelation of Crude Oil from a Biphasic Mixture of Oil and Salt Solution:

In a typical procedure, 0.5 mL of crude oil and 0.5 mL of 3.5% of NaCl solution (equivalent salt concentration to that of sea water) were taken in a sample tube to which required of the gelator compound of Formula I was added. The gelator was then solubilized in this two-phase solution by heating. After the mixture was cooled to room temperature, the crude oil layer was gelated, keeping the water layer intact in the liquid state. The same process was followed for other oils like CRN, SRN and diesel.

TABLE 5

Gelation abilities of compound of formula I in various oil-sea water mixture

| | Compound | | | | | | | | | | | | |
|---|---|---|---|---|---|---|---|---|---|---|---|---|---|
| | 1 | | 2 | | 3 | | 4 | | 5 | | 6 | | 7 | |
| | MGC (% w/v) | MUC | MGC (% w/v) | MUC | MGC (% w/v) | MUC | MGC (% w/v) | MUC | MGC (% w/v) | MUC | MGC (% w/v) | MUC | MGC (% w/v) | MUC |
| Crude-Sea Water | 2 | 50 | 2.3 | 43 | 2.3 | 43 | 2.6 | 38 | 1 | 100 | 1.25 | 80 | 1.5 | 66 |
| CRN-Sea Water | 1.2 | 83 | 1.3 | 76 | 1.3 | 76 | 1.4 | 71 | 0.5 | 200 | S | ... | P | ... |
| SRN-Sea Water | 1 | 100 | 1.2 | 83 | 1.2 | 83 | 1.3 | 76 | 0.4 | 250 | 1.3 | 76 | P | ... |
| Diesel-Sea water | 1.2 | 83 | 1.2 | 83 | 1.3 | 76 | 1.4 | 71 | 0.4 | 250 | 0.55 | 181 | 1.6 | 62 |

MGC = Minimum Gelation Concentration,
MUC = Minimum Uptake Capability,
S = Soluble,
I = Insoluble,
P = Precipitate Oil Selective gelation of petroleum products from a biphasic mixture of oil and sea water was also performed and the results are tabulated in Table 5. Gelator compounds were able to gelate exclusively the oil phase without altering the sea water phase during performance evaluation gelation experiments. Comparison of the results from Table 4 and Table 5 led us to conclude that even under highly saline conditions, negligible changes/effect on gelation properties (MCG & MUC) were observed. This observation indicated the strength and capability of the organogelator towards the gelation preference for organic phase even under extreme conditions.

Advantages Gained in the Example Illustrative Process in this Subject Matter:

Environmentally benign amino acid based phase selective gelator has been developed for oil phase gelation from a mixture of oil and water. The gelators efficiently work even at a very low concentration and at room temperature. The gelators find application in marine oil spill recovery. Oil from the gel can be recovered and gel can be recycled and reused for number of cycles without loss of activity.

Although the subject matter has been described in considerable detail with reference to certain examples and implementations thereof, other implementations are possible. As such, the spirit and scope of the appended claims should not be limited to the description of the preferred examples and implementations contained therein.

We claim:

1. A compound having the Formula:

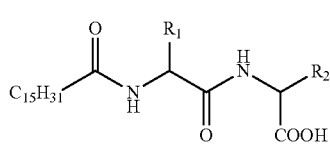

Formula I wherein,
$R_1$ is substituted $C_1$ to $C_{10}$ alkyl;
$R_2$ is substituted $C_1$ to $C_{10}$ alkyl.

2. The compound as claimed in claim 1, wherein $R_1$ and $R_2$ are independently selected from $C_1$ to $C_5$ alkyl substituted with $C_1$ to $C_3$ alkyl, $C_5$-$C_{10}$ aryl, $C_6$-$C_{10}$ heteroaryl, or a heteroatom selected from the group consisting of O, N, and S, wherein the heteroatom is further substituted with $C_1$ to $C_3$ alkyl, $C_5$-$C_{10}$ aryl, or $C_6$-$C_{10}$ heteroaryl.

3. The compound as claimed in claim 1, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or a heteroatom selected from the group consisting of O, N, and S, wherein the heteroatom is further substituted with $C_1$ to $C_2$ alkyl, $C_5$-$C_{10}$ aryl, or $C_6$-$C_{10}$ heteroaryl.

4. The compound as claimed in claim 1, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or a heteroatom selected from the group consisting of O, N, and S, wherein the heteroatom is further substituted with $C_1$ to $C_2$ alkyl.

5. The compound as claimed in claim 1, wherein $R_1$ and $R_2$ are independently selected from $C_1$ to $C_3$ alkyl substituted with $C_1$ to $C_2$ alkyl, $C_5$-$C_8$ aryl, $C_6$-$C_{10}$ heteroaryl, or S further substituted with $C_1$ to $C_2$ alkyl, wherein both $R_1$ and $R_2$ are not $C_1$ to $C_3$ alkyl substituted with S further substituted with $C_1$ to $C_2$ alkyl.

6. The compound as claimed in claim 1, wherein $R_1$ and $R_2$ are independently selected from $C_1$ to $C_2$ alkyl substituted with $C_1$, $C_6$ aryl, $C_8$ heteroaryl with N as the heteroatom, or S further substituted with $C_1$ alkyl, wherein both $R_1$ and $R_2$ are not $C_1$ to $C_2$ alkyl substituted with S further substituted with $C_1$ alkyl.

7. The compound as claimed in claim 1, wherein $R_1$ and $R_2$ are independently selected from $C_1$ to $C_3$ alkyl substituted with $C_1$ to $C_2$ alkyl, or S further substituted with $C_1$ to $C_2$ alkyl, wherein both $R_1$ and $R_2$ are not $C_1$ to $C_3$ alkyl substituted with S substituted with $C_1$ to $C_2$ alkyl.

8. The compound as claimed in claim 1, wherein $R_1$ is $C_1$ to $C_3$ alkyl substituted with $C_1$ to $C_2$ alkyl, and $R_2$ is $C_1$ to $C_3$ alkyl substituted with S further substituted with $C_1$ to $C_2$ alkyl.

9. The compound as claimed in claim 1, wherein $R_1$ is $C_2$ alkyl substituted with $C_1$ alkyl, and $R_2$ is $C_2$ alkyl substituted with S further substituted with $C_1$ alkyl.

10. A process for preparing the compound of claim 1, comprising
   (a) coupling the methyl ester of an amino acid with palmitic acid chloride in dry chloroform in presence of triethylamine;
   (b) purifing the ester-protected long-chain amide or monopeptide;
   (c) hydrolyzing the product using NaOH in MeOH followed by acidification using HCI to produce a monopeptide carboxylic acid;
   (e) coupling the monopeptide carboxylic acid with another methyl ester protected amino acid using DCC in dry dichloromethane (DCM) in presence of HOBT and DMAP;
   (f) hydrolysis the product using NaOH in MeOH followed by acidification using HCI.

\* \* \* \* \*